United States Patent [19]

Monte

[11] Patent Number: 4,931,432

[45] Date of Patent: Jun. 5, 1990

[54] DIETARY VACCINE FOR INHIBITING METABOLISM OF METHANOL

[76] Inventor: Woodrow C. Monte, 542 W. 16th St., Tempe, Ariz. 85281

[21] Appl. No.: 290,364

[22] Filed: Dec. 29, 1988

Related U.S. Application Data

[63] Continuation of Ser. No. 47,673, May 6, 1987, Pat. No. 4,834,981.

[51] Int. Cl.$^5$ .......................................... A61K 31/715
[52] U.S. Cl. .................................... 514/54; 424/451; 424/452
[58] Field of Search .................. 514/54; 424/451, 452

[56] References Cited

U.S. PATENT DOCUMENTS

| | | | |
|---|---|---|---|
| 3,897,547 | 7/1975 | Adams et al. | 424/451 |
| 4,388,324 | 6/1983 | Horrobin | 514/282 |
| 4,535,093 | 8/1985 | Horrobin | 514/552 |

Primary Examiner—Ronald W. Griffin
Assistant Examiner—Pamela S. Webber
Attorney, Agent, or Firm—Tod R. Nissle

[57] ABSTRACT

Apparatus and a method for inhibiting the metabolism of methanol in a human. The apparatus comprises carrier means for a source of ethanol. The carrier means, when combined with a source of ethanol and introduced in the digestive tract of a human being, permits the gradual time release of ethanol from the dietary vaccine into the digestive tract for absorption into the blood system of an individual. The method comprises introducing the ethanol charged carrier means in the digestive tract of an individual.

11 Claims, No Drawings

DIETARY VACCINE FOR INHIBITING METABOLISM OF METHANOL

This is a continuation of U.S. application Ser. No. 047,673, filed May 6, 1987, now U.S. Pat. No. 4,834,981.

This invention pertains to apparatus and methods for preventing in humans the metabolism of methanol to form the toxic metabolites formaldehyde and formic acid.

More particularly, the invention pertains to a benign metabolic dietary vaccine which can be introduced at any point in the digestive tract of an individual to protect the individual from blindness, other visual disturbances, neuritis, headaches, dizziness, severe depression, myocardial hypertrophy and activation of the reticuloendothelial system which can result from the metabolism of methanol by the body.

In a further respect, the invention pertains to a dietary vaccine which, by continually releasing in the digestive tract minor effective amounts of an anti-metabolic substance which is absorbed into the blood stream, protects an individual from various pollutant sources of methanol.

Methanol is one of the most widespread, insidious toxicants encountered in modern civilization. Common sources of methanol are liquor, cigarette smoke, fumes from gasoline to which methanol has been added to increase octane, ditto machines, and Nutrasweet®, Nutrasweet®, the new artificial sweetner which is a generally accepted substitute for saccharine, is a small molecule made up of three components: Phenylalanine, aspartic acid, and methanol (wood alcohol). Methanol may be derived in some individuals from metabolic processes involving intestinal flora. For instance, the action of Pectin-methylesterase on dietary pectins, can liberate methanol.

Methanol is a toxicant which has no therapeutic properties. The ingestion of two teaspoons can be lethal in humans. Methyl alcohol produces the Methyl Alcohol Syndrome, consistently, only in humans and in no other animal. There is a clear different between "toxicity", which can be produced in every living thing, and the methyl alcohol "toxic syndrome". The greater toxicity of methanol to man is deeply rooted in the limited biochemical pathways available to humans for detoxification. The loss of uricase (EC 1.7.3.3.), formyl-tetrahydrofolate synthetase (EC 6.3.4.3.) and other enzymes during evolution sets man apart from all animals including the monkey. Humans suffer "toxic syndrome" at a minimum lethal methanol dose of less than 1 gm/kg, much less than that of monkeys, 3–6 gm/kg.

The United States Environmental Protection Agency in their Multimedia Environmental Goals for Environmental Assessment recommends a minimum acute toxicity concentration of methanol in drinking water at 3.9 parts per million, with a recommended limit of consumption below 7.8 mg/day. This report clearly indicates that methanol:

". . . is considered a cumulative poison due to the low rate of excretion once it is absorbed. In the body, methanol is oxidized to formaldehyde and formic acid; both of these metabolites are toxic."

The most characteristic symptoms of methyl alcohol poisoning in humans are the various visual disturbances which can occur. These symptoms include misty vision, progressive contraction of visual fields (tunnel vision), mist before the eyes, blurring of vision, and obscuration of vision. Other methyl alcohol poisoning symptoms include headache, ear buzzing, dizziness, nausea, unsteady gait, gastrointestinal disturbances, weakness, vertigo, chills, memory lapses, behavioral disturbances, neuritis, and numbness and shooting pains in the lower extremities, hands and forearms. In fatal cases, the liver, kidneys and heart may show parenchymatous degeneration, while the lungs show desquamation of epithelium, emphysema, edema, congestion and bronchial pneumonia.

Ethanol is well known as a desperate cure for severe cases of methanol poisoning. The ethanol is administered intravenously in substantial amounts sufficient to inhibit the metabolism of methanol to formaldehyde and formic acid. The amounts of ethanol intravenously administered are, alone, sufficient to cause intoxication of the patient, but this effect is accepted in order to prevent the death of or severe injury to the patient.

When ethanol is present in the body together with methanol, the body generally first selectively metabolizes the ethanol, permitting the body to remove methanol through the lungs and urine. However, if concentration of ethanol in the body is too low, the body can metabolize methanol into formaldehyde and formic acid.

Most individuals do not ingest lethal amounts of methanol over short periods of time but are, during their lifetime, instead exposed to dietary and environmental sources containing moderate or small amounts of methanol. Since methanol is a cumulative toxin, such sources pose a threat to the physical well being of an individual. For example, an average aspartame-sweetened beverage has an aspartame content of about 555 mg/liter, and, therefore, has a methanol content of 56 mg/liter (56 ppm). If a child weighing twenty five kilograms consumes on a warm day, after exercising, two-thirds of a two-liter bottle of soft drink sweetened with aspartame, that child consumes over 732 mg of aspartame (29 mg/kg). This alone exceeds the safe daily aspartame consumption level specified by the Food and Drug Administration. The child would absorb over 70 mg of methanol from the soft drink. This is almost ten times the Environmental Protection Agency's recommended daily limit of consumption for methanol.

There is apparently presently no method for protecting an individual from the metabolism of cumulative minimal amounts of environmental methanol pollutants daily ingested into the body. The intravenous administration of ethanol is acceptable in severe cases of methanol poisoning because of the desperateness of such cases. Such administration of ethanol is not feasible under normal day-to-day living circumstances because of the intoxicating effect of ethanol and because of the impracticality of repeated intravenous administration of a substance. Further, in order to provide ethanol protection in the body for a reasonable period of time after the intravenous administration of ethanol, an intoxicating concentration of ethanol must be directed into the blood stream.

Oral consumption of ethanol is not a desirable method for treating methanol poisoning because it is difficult to control the rate that ethanol is absorbed in the blood stream, and because, unless a container of ethanol is constantly carried on the person, an intoxicating amount of ethanol must be consumed to protect a person for a reasonable period of time after ethanol has been ingested.

Therefore, it would be highly desirable to provide a method for protecting an individual from methanol which he or she daily ingests from dietary and environmental pollutant sources, and which could be readily implemented by an individual without requiring the utilization of catheters or other medical equipment.

It would also be highly desirable to provide a method which would, after a single use, provide an individual over an extended period of time with continuous protection from ingested methanol.

I have discovered a new metabolic dietary vaccine composition and method for administering the composition which enables an individual to readily protect himself from methanol ingested or inhaled from various environmental pollutant sources. The dietary vaccine composition inhibits the metabolism of methanol by the body to form formaldehyde and formic acid. The composition comprises a source of ethanol and carrier means for the ethanol source. The carrier means permits the gradual release over time of ethanol into the digestive tract of an individual. The ethanol is released in minor effective amounts sufficient to inhibit the metabolism of methanol in the body and sufficient to avoid intoxicating the individual.

In another embodiment of the invention, I provide a method for preventing the metabolism of methanol in the body to form formaldehyde and formic acid. The method comprises the steps of introducing in the digestive tract of an individual a dietary vaccine comprising a source of ethanol and carrier means, the carrier means permitting the gradual release of ethanol into the digestive tract in minor effective amounts sufficient to inhibit the metabolism of methanol in the body and sufficient to avoid the intoxication of the individual by the ethanol.

It is presently preferred that the carrier means release ethanol into the digestive tract at a rate sufficient to maintain a concentration of ethanol in the blood stream generally in the range of ten to fifty parts per million (ppm). However, the release of ethanol from the carrier means can be at a rate sufficient to maintain a concentration of one to two hundred and fifty parts per million ethanol in the blood stream. If ethanol is released from the carrier means at a rate sufficient to maintain a concentration in the blood stream of greater than 1,000 ppm, the individual will probably become intoxicated. If the concentration of ethanol in the blood stream is greater than 200-700, then methanol generally is not removed from the body through the urine and breath.

The source of ethanol can be administered into the digestive tract from within carrier means comprising a capsule having a dialytic wall with pores which permit ethanol carried in the capsule to slowly bleed through the pores into the digestive tract. The ethanol can be mixed with propylene glycol, glycerol, water, potassium or sodium stearate (which is known to deactivate pectin-methylesterase) or other solid or liquid substances which function as carrier means to slow or increase the rate of diffusion of ethanol through the dialytic wall of the capsule. The capsule can be orally, suppositorily, or surgically introduced in the digestive tract. The dialytic wall of the capsule presently preferably comprises a cellophane or polycarbonate film having pores approximately 10 Angstroms in diameter. The width of each pore opening can vary, but is preferably in the range of 5 to 30 Angstroms. The dialytic film or wall is preferably resistant to degradation by the digestive system for a period of time necessary to permit all or nearly all of the ethanol carried within the dialytic film to gradually bleed through the pores into the digestive tract.

In certain cases, the wall of the capsule or carrier means can be rapidly destroyed by the digestive system. For instance, a solution of ethanol could be mixed or chemically combined or bound with a thickener or some other carrier composition which would slow the release of ethanol into the digestive tract. In this instance, the capsule wall or coating enclosing the ethanol mixture need not be dialytic or resistance to digestive system fluids, but could be comprised of a gelatin which would rapidly dissolve in the digestive tract to release the ethanol—thickener mixture.

The membrane wall or film encapsulating a source of ethanol is preferably comprised of a physiologically nontoxic material. Since ethanol is volatile and rapidly evaporates when exposed to the atmosphere, capsules carrying ethanol are, prior to being stored for later use, preferably coated with a material which prevents or slows evaporation of ethanol into the atmosphere. Alternatively, the capsules can be stored in a container which maintains a vapor pressure equal to or greater than that of the ethanol, or, may be stored in a solution which has equivalent ethanol content and which does not tend to break down or alter the chemical composition of the ethanol source and its carrier means.

When the carrier capsule or tablet is administered orally, it may be desirable that it be coated with an enteric substance so the capsule will not be destroyed prior to its reaching the lower intestinal tract. If a capsule or tablet having a dialytic film is not utilized and a source of ethanol is simply mixed or chemically combined with a carrier substance which slows the release of ethanol in the intestinal tract, then it is preferred that the ethanol source–carrier substance mixture be resistant to stomach digestive chemicals so the ethanol will not be completely released in the stomach.

Ethanol is readily absorbed into the body at any point along the digestive tract, including the stomach lining and large and small intestines. Therefore, the carrier means can be formed to permit the gradual release of ethanol during the entire time period required for the ethanol dietary vaccine to traverse the digestive tract.

The dietary vaccine composition of the invention permits the gradual controlled release into the blood stream of minor effective amounts of ethanol which act to prevent the metabolism of methanol and which, at the same time, are not either sufficient to cause intoxication of an individual or sufficient to prevent methanol from being removed by the body through the breath and urine. The dietary vaccine composition of the invention can be readily ingested by an individual without requiring the utilization of intravenous or other medical equipment.

An alcohol such as ethanol has never been combined with a time release carrier means.

An alcohol such as ethanol has never been introduced into the digestive tract of an individual for gradual release therealong as a dietary vaccine.

An alcohol such as ethanol has never been utilized as a universal preventitive to protect an individual from all environmental sources of pollutant methanol.

In use, a source of ethanol is combined with time release lease carrier means and is introduced into the digestive tract of an individual. After the ethanol—time release carrier means unit has been introduced in the digestive tract and a sufficient amount of time has passed for the desired portion of all of the ethanol carried in the unit to be released into the intestine, another ethanol—carrier means unit can be introduced in the digestive tract of an individual. Units can be introduced in the digestive tract as often as necessary to keep the concentration of ethanol in the blood stream at a selected level.

A particular advantage of the invention is that it provides—with a single administration of an ethanol—carrier means capsule or unit, an extended period of protection from metabolism by the body of methanol.

Sources of ethanol include ethyl alcohol, ethyl esters of various chemicals—for example pectin ethylester—that metabolize in the body in such a way as to slowly liberate ethanol upon clevage of the ethyl ester, and include microorganisms that can survive within a dialytic capsule or other ethanol source carrier means and either convert through fermentation various dietary carbohydrates into ethanol or otherwise produce ethanol through the microorganisms' own metabolic processes.

As used herein, the term "apparatus" refers to liquid, semi-liquid, and/or solid material carrier means utilized to carry ethanol into the digestive tract of an individual and release over time the ethanol carried by the carrier means. For example, the capsules described in Examples 5 to 10 comprise apparatus or carrier means constructed and used in accordance with the invention.

As used herein, the term "dietary" refers to a composition or apparatus which is, in use, introduced in the stomach and/or intestinal tract of an individual.

The following examples are presented, not by way of limitation of the scope of the invention, but to illustrate to those skilled in the art, the practice of various of the presently preferred embodiments of the invention and to distinguish the invention from the prior art.

EXAMPLE 1

A 43 year-old male subject, five feet seven inches high, weighing 220 pounds, had complained of severe headaches, vertigo, nausea and blurring of vision within hours of consumption of a can of diet soft drink containing NUTRASWEET sweetener. NUTRASWEET is an artificial sweetener which releases approximately 10% by weight of methanol during digestion. The subject was in good health and was not taking any prescription drugs or other medications. When the subject consumed twelve ounces of saccharine sweetened fluid, the subject did not exhibit the headaches and other adverse symptoms noted above. The subject had been a teacher in a public school system and recalled experiencing the same symptoms subsequent to the use of inadequately ventilated duplication equipment which required spirit fluid that contained over 50% methanol.

EXAMPLE 2

The male subject of EXAMPLE 1 consumed two grams of pure NUTRASWEET There is over 1.7 grams of NUTRASWEET sweetener in a six pack of diet Orange Soda soft drink twelve ounce cans. The NUTRASWEET sweetener was ingested in four gelatin capsules Within one hour after the two grams of pure NUTRASWEET sweetener had been consumed, the subject was experiencing a headache and dizziness. A sample of the subject's blood was taken using the finger prick technique, excluding alcohol swabbing of the finger prior to lancing. The blood methanol concentration of the subject had risen to over 1.5 parts per million. Samples of the subjects blood were thereafter taken at thirty minute intervals. An hour and a half after consumption of the pure NUTRASWEET, the blood methanol concentration peaked at two parts per million. Shortly after the blood methanol concentration peaked at two parts per million, the subject complained of nausea and blurred vision. These symptoms, along with the headache and dizziness, persisted for four hours prior to subsiding. After the symptoms had subsided, the methanol levels in the blood of the subject were again undetectable.

The blood samples from the male subject were tested for methanol and ethanol using a Varian Aerograph Model 3700 gas chromatograph equipped with a flame ionization detector and a six foot × two millimeter interior diameter glass column packed with a 60/80 Carbopack B coated with Carbowax 20M. The column was equipped with a precolumn and helium was the carrier gas at a flow rate of 20 ml/min. The whole blood samples were each diluted with an internal standard solution of n-propanol and injected directly onto the column. The column was operated isothermally at a temperature of 75° C. The peak areas were calculated by a Hewlett-Packard 3390 A integrator. Under normal conditions, i.e., prior to consumption of NUTRASWEET sweetener, of methanol, or of ethanol, the level of ethanol and methanol in the subject's blood was undetectable.

EXAMPLE 3

Example 2 is repeated, except that the subject consumes a six pack of diet Orange Soda soft drink twelve ounce cans over one hour period instead of consuming two grams of pure NUTRASWEET sweetener. Similar results were obtained.

EXAMPLE 4

Example 2 is repeated, except that the subject consumes two hundred milliliters of a one gram per liter solution of methanol instead of consuming two grams of pure NUTRASWEET sweetener. The blood methanol concentration of the subject peaked at 3.2 parts per million within one half hour after consumption of the solution The symptoms of headache, dizziness, nausea and blurred vision occurred one hour after consumption of the test liquid and subsided approximately two and one half hours after the solution of methanol was consumed.

EXAMPLE 5

The following are combined and heated until the solution clears and the sodium stearate dissolves:
Absolute ethanol : 84.00 grams
Sodium stearate : 4.40 grams
Water : 11.60 grams
No. 000 gelatin capsules are filled with the heated, clear solution and allowed to cool until the solution has jelled The filled, cooled gelatin capsules are coated with a protective time release azopolymer film by dipping into a 15% Methylene chloride solution of a copolymner of styrene and hydroxyethylmethacrylate cross-linked with divinylazobenzene and allowing the methylene chloride solvent to evaporate. The resulting azopolymer coating is, when the capsule is ingested, attacked by the indigenous microflora in the large intestines. The microflora reduce the azo bonds and allow the slow release of ethanol. The chloride copolymer solution is produced by mixing 140 grams of styrene, 860 grams of hydroxyethylmethacrylate and 20 grams of divinylazobenzene and using conventional methods to polymerize with twenty grams of benzoyl peroxide as the initiator. Unreacted monomers are removed by repeated re-precipitation from chloroform solution by the addition of hexane.

EXAMPLE 6

Gelatin capsules are produced in accordance with EXAMPLE 5, except that the capsules are filled with an undiluted absolute ethanol solution instead of the warm, clear absolute ethanol—sodium stearate—water solution of EXAMPLE 5.

EXAMPLE 7

No. 000 gelatin capsules are filled with the warm, clear absolute ethanol—sodium stearate—water solution of EXAMPLE 5. After the solution has jelled, the gelatin capsules are transferred to a coating pan and coated with cellulose acetate phthalate. Seven coats of cellulose acetate phthalate are applied and standard USP Disintegration Testing Apparatus is used to test the quality of the coatings.

EXAMPLE 8

The warm, clear absolute ethanol—sodium stearate—water solution of EXAMPLE 5 is prepared and used to fill sacks made from Dialyzer tubing. After the water solution has cooled and jelled, the Dialyzer tubing sacks are coated with a protective time release azopolymer film in the manner described in EXAMPLE 5.

EXAMPLE 9

Sacks made from Dialyzer tubing are filled with an undiluted absolute ethanol solution. The Dialyzer tubing sacks are coated with a protective time release azopolymer film in the manner described in EXAMPLE 5.

EXAMPLE 10

Sacks made from Dialyzer tubing are filled with an undiluted absolute ethanol solution. The Dialyzer tubing sacks are coated with cellulose acetate phthalate in the manner described in EXAMPLE 7.

EXAMPLE 11

500 grams of polygalacturonide obtained from citrus pectin and 1500 grams of absolute ethyl alcohol are refluxed under pressure at 65° C. rather than at the reflux temperature of ethanol. After ninety hours the polyethyl compound left after evaporation of the ethanol contains about 11.7% ethoxy group and is about 50% esterified. The polyethyl compound can be administrated as an ethanol source in place of the absolute ethanol—sodium stearate—water solution of EXAMPLE 5.

EXAMPLE 12

A 43 year old male subject was selected. The subject was five feet seven inches high, weighed 220 pounds, was in good health and was not taking any prescription drugs or other medications. The ethanol and methanol levels in the subject were tested using the blood sampling process of Example 2. There initially were no detectable levels of ethanol and methanol in the blood stream. The subject consumed at one sitting four of the ethanol capsules produced in the manner described in EXAMPLE 5. Three hours later the subject consumed two grams of NUTRASWEET sweetener. After consuming the four capsules, the subject's blood was tested at hour intervals for concentration levels of ethanol and methanol. The ethanol level in the subject's blood peaked at 14.6 parts per million three hours after ingestion of the four ethanol capsules Eight hours after the capsules were ingested, the ethanol concentration in the blood was 5.7 parts per million. Six hours after the NUTRASWEET was consumed, the concentration of blood methanol was undetectable. At no time did the subject experience headache, dizziness, nausea, and/or vision blurring.

EXAMPLE 13

The process of EXAMPLE 12 is repeated, except that four ethanol No. 000 gelatin capsules filled with 1 gram/liter aqueous methanol solution are utilized. Similar results are obtained, with the maximum level of methanol in the blood being 3.9 ppm.

EXAMPLE 14

The process of EXAMPLE 2 is repeated, except that the subject is a 23 year old female who is in good health, has a height of five feet one inch, weighs one hundred pounds, and is not taking any prescription drugs or other medication. Similar results are obtained.

EXAMPLE 15

The process of EXAMPLE 12 is repeated except that only two ethanol capsules are consumed by the subject. Similar results are obtained.

EXAMPLE 16

The process of EXAMPLE 12 is repeated except that five to twenty ethanol capsules are consumed by the subject. Similar results are obtained.

EXAMPLE 17

The process of EXAMPLE 12 is repeated except that six cans of twelve ounce diet soft drink beverage containing a total of 1.7 grams of NUTRASWEET are consumed instead of the two grams of pure NUTRASWEET. The cans are consumed over a period of one hour. Similar results are obtained.

EXAMPLE 18

The process of EXAMPLE 12 is repeated, except that the subject is a 27 year old female who is in good health, has a height of five feet three inches, weigh one hundred and ten pounds, and is not taking any prescription drugs or other medication. Similar results are obtained.

EXAMPLE 19

The process of EXAMPLE 12 is repeated, and when the levels of methanol and ethanol in the blood are tested, the levels of formaldehyde and formic acid, the metabolites of methanol, are also tested. The levels of formaldehyde and formic acid are undectable during all blood tests.

EXAMPLE 20

The process of EXAMPLE 2 is repeated, and when the level of methanol in the blood is tested, the levels of formaldehyde and ethanol in the blood are tested. One hour after the NUTRASWEET is consumed levels of formaldehyde and formic acid in the blood stream are not detectable.

EXAMPLE 21

The process of EXAMPLE 12 is repeated, except that a sugar or starch fermented in the presence of yeast is used in place of the absolute ethanol—sodium stearate—water solution to provide a source of ethanol. Similar results are obtained.

EXAMPLE 22

The process of EXAMPLE 12 is repeated, except that fermented blackstrap molasses is used in place of the absolute ethanol—sodium stearate—water solution to provide a source of ethanol. Similar results are obtained.

EXAMPLE 23

The process of EXAMPLE 12 is repeated, except that fermented potatoes or a fermented grain is used in place of the absolute ethanol—sodium stearate—water solution to provide a source of ethanol. Similar results are obtained.

The EC 1.7.3.3 designation earlier used herein to describe the uricase enzyme is an official international designation utilized to differentiate enzymes.

Ethanol derived from petroleum products can also be utilized in the practice of the invention.

The dietary vaccine of the invention can be ingested with or after the ingestion of methanol or of substances which are metabolized into methanol by the body. Maintaining a concentration of at least one ppm ethanol in the blood stream appears to generally prohibit metabolism of methanol by the body. Preferably, the vaccine is ingested prior to the ingestion of methanol or a methanol producing substance so that a concentration of ethanol of at least one ppm can be established in the blood stream to protect an individual against the metabolism of methanol by his body.

As utilized herein, absolute ethanol indicates grain alcohol which has been passed over a molecular sieve Grade 512 Type 4A (4–8 mesh) distributed by Matheson, Coleman and Bell Company. The molecular sieve markedly reduces the amount of methanol and water in the grain alcohol.

Having described my invention in such terms as to enable those skilled in the art to understand and practice it, and having identified the presently preferred embodiments and best mode thereof, I claim:

1. A dietary vaccine introduced in the digestive tract of an individual to inhibit the metabolism of methanol by the human body to form formaldehyde and formic acid, said dietary vaccine comprising, in combination,
   (a) at least one source of ethanol selected from the class consisting of ethyl alcohol and a polyethyl compound, said polyethyl compound being obtained by reflexing polygalacturonide and absolute ethyl alcohol; and,
   (b) capsule carrier means other than gelatin capsule carrier means for said source of ethanol, said carrier means, when introduced in the digestive tract of a human being, permitting, while said carrier means moves along at least a selected portion of said digestive tract, the continuous release of ethanol from said carrier means into said digestive tract for absorption into the blood system of the individual in minor effective amounts sufficient to
   maintain a concentration of ethanol in the blood stream of less than two hundred and fifty parts per million ethanol,
   inhibit the metabolism of methanol by the body, and
   avoid the intoxication of said individual by said ethanol.

2. A method for inhibiting the metabolism by the human body of methanol to form formaldehyde and formic acid, said method including the steps of
   (a) producing a metabolic dietary vaccine said dietary vaccine including
      (i) at least one source of ethanol selected from the class consisting of ethyl alcohol and a polyethyl compound, said polyethyl compound being obtained by reflexing polygalacturonide and absolute ethyl alcohol, and,
      (ii) carrier means other than gelatin capsule carrier means for said source of ethanol introduced in the digestive tract of an individual, permitting the gradual release of ethanol from said dietary vaccine into the digestive tract for absorption into the blood stream of the individual in minor effective amounts sufficient to
      inhibit the metabolism of methanol by the individual's body, and
      generally avoid intoxication of the individual; and
   (b) introducing said dietary vaccine in the digestive tract of an individual, said carrier means, when introduced in and moving along at least a selected portion of said digestive tract, permitting the continuous release of ethanol from said carrier means into the digestive tract for absorption into the blood stream of the individual in minor effective amounts sufficient to
      establish a concentration of ethanol in the blood stream in the range of one part to two hundred and fifty parts per million ethanol,
      maintain a concentration of ethanol in the blood stream in the range of one part to two hundred and fifty parts per million ethanol,
      inhibit the metabolism of methanol by the individual's body, and
      avoid intoxication of the individual by said ethanol.

3. The dietary vaccine of claim 1 wherein said source of ethanol is selected from the class consisting of fermented blackstrap molasses, fermented potatoes, fermented grain, fermented starch and fermented sugar.

4. The method of claim 2 wherein said source of ethanol is selected from the class consisting of fermented blackstrap molasses, fermented potatoes, fermented grain, fermented starch and fermented sugar.

5. The dietary vaccine of claim 1 wherein said capsule carrier means comprises dialyzer tubing.

6. The method of claim 2 wherein said capsule carrier means comprises dialyzer tubing.

7. The dietary vaccine of claim 1 wherein said carrier means includes a capsule having a wall including pores formed therethrough each with a width in the range of five to thirty Angstroms.

8. The dietary vaccine of claim 7 wherein said capsule is coated with a methylene chloride solution of a copolymer of styrene and hydroxyethylmethacrylate cross-linked with divinylazobenzene.

9. The dietary vaccine of claim 1 wherein said concentration of ethanol in the blood stream is maintained for a period of time greater than three hours.

10. The method of claim 2 wherein said concentration of ethanol is maintained in the blood stream for a period of time greater than three hours.

11. A method for inhibiting the metabolism by the human body of methanol to form formaldehyde and formic acid, said method including the steps of
   (a) producing a metabolic dietary vaccine, said dietary vaccine including
      (i) grain alcohol, the methanol in said grain alcohol having been substantially removed therefrom, and
      (ii) carrier means other than gelatin capsule carrier means for said grain alcohol; and,
   (b) introducing said dietary vaccine in the digestive tract of an individual, said carrier means, when introduced in and moving along at least a selected portion of said digestive tract, permitting the continuous release of ethanol from said carrier means into the digestive tract for absorption into the blood stream of the individual in minor effective amounts sufficient to
   establish a concentration of ethanol in the blood stream in the range of ten parts to fifty parts per million ethanol,
   maintain a concentration of ethanol in the blood stream in the range of ten parts to fifty parts per million ethanol,
   inhibit the metabolism of methanol by the individual's body, and
   avoid intoxication of the individual by said ethanol.

* * * * *